United States Patent
Stutzman

(10) Patent No.: US 9,549,563 B2
(45) Date of Patent: Jan. 24, 2017

(54) SWEET TART ENERGY TABLET

(71) Applicant: KickAss Candy LLC, Overland Park, KS (US)

(72) Inventor: Todd Stutzman, Overland Park, KS (US)

(73) Assignee: KickAss Candy LLC, Overland Park, KS (US)

(*) Notice: Subject to any disclaimer, the term of this patent is extended or adjusted under 35 U.S.C. 154(b) by 0 days.

(21) Appl. No.: 14/353,289

(22) PCT Filed: Oct. 24, 2012

(86) PCT No.: PCT/US2012/061752
§ 371 (c)(1),
(2) Date: Apr. 21, 2014

(87) PCT Pub. No.: WO2013/063163
PCT Pub. Date: May 2, 2013

(65) Prior Publication Data
US 2014/0255463 A1    Sep. 11, 2014

Related U.S. Application Data

(60) Provisional application No. 61/550,546, filed on Oct. 24, 2011.

(51) Int. Cl.
| | |
|---|---|
| *A23G 3/48* | (2006.01) |
| *A23L 2/395* | (2006.01) |
| *A23L 2/52* | (2006.01) |
| *A23L 2/56* | (2006.01) |
| *A61K 9/20* | (2006.01) |
| *A61K 31/522* | (2006.01) |

(52) U.S. Cl.
CPC ............... *A23G 3/48* (2013.01); *A23L 2/395* (2013.01); *A23L 2/52* (2013.01); *A23L 2/56* (2013.01); *A23L 27/84* (2016.08); *A23L 27/86* (2016.08); *A61K 9/2018* (2013.01); *A61K 9/2095* (2013.01); *A61K 31/522* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,900,416 A | 5/1999 | Markson | |
| 6,953,593 B2 | 10/2005 | Kuhrts | |
| 7,612,073 B2 | 11/2009 | Oppenheimer | |
| 2005/0232988 A1 | 10/2005 | Venkatesh et al. | |
| 2006/0094734 A1 | 5/2006 | Newman | |
| 2006/0134300 A1 | 6/2006 | Newman | |
| 2006/0165614 A1 | 7/2006 | Nelson et al. | |
| 2010/0286286 A1* | 11/2010 | Ikeda et al. ............... | 514/770 |
| 2011/0053942 A1 | 3/2011 | Fujiwara et al. | |

FOREIGN PATENT DOCUMENTS

WO    WO 00/13523    * 3/2000

OTHER PUBLICATIONS

English translation of JP 2005-343800 (Dec. 15, 2005).*
English Abstract of JP 2005-343800 (Dec. 15, 2005).*
International Searching Authority, Written Opinion of the International Searching Authority, Feb. 1 2013, 5 pages.
International Searching Authority, International Search Report, Feb. 1, 2013, 4 pages.
International Preliminary Examining Authority, International Preliminary Report on Patentability, Sep. 19, 2013, 8 pages.
Applicant, Demand, Oct. 24, 2012, 3 pages.
Applicant, Amendment under Article 34, Oct. 24, 2012, 5 pages.
Wandrey et al. Chapter 3: "Materials for Encapsulation", Encapsulation Technologies for Active Food Ingredients and Food Processing, DOI 10.1007/978-1-4419-1008-0_3, 2010, pp. 31-100, Springer Science+Business Media, LLC.
Majeti, Satyanarayana. International Patent Application Publication No. WO1996000070 A1, "Treatment of nicotine craving and/or smoking withdrawal symptoms with an oral composition containing nicotine and caffeine or xanthine", Jan. 4, 1996.

* cited by examiner

*Primary Examiner* — David J Blanchard
*Assistant Examiner* — Garen Gotfredson
(74) *Attorney, Agent, or Firm* — D'Hue Law LLC; Cedric A. D'Hue

(57)    ABSTRACT

An energy tablet and method of manufacturing the same that successfully masks the bitter taste of caffeine which has precluded popularity of chewable energy tablets in the past.

16 Claims, 1 Drawing Sheet

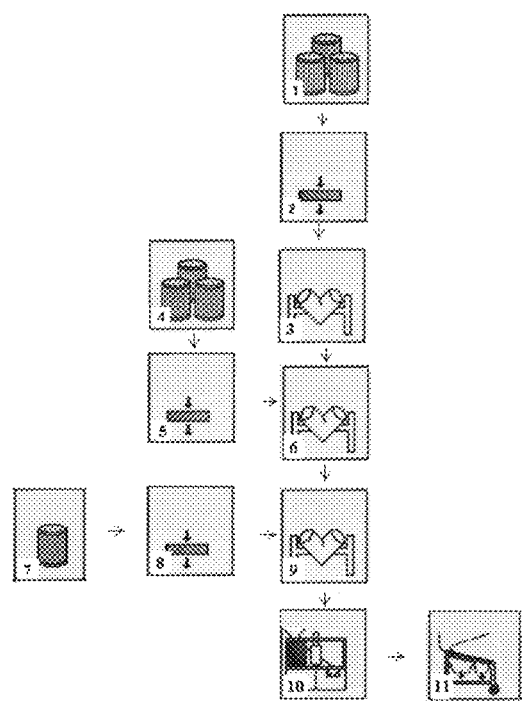

SWEET TART ENERGY TABLET

FIELD

The present disclosure includes an energy tablet and method of manufacturing the same that successfully makes the energy tablet palatable by masking the bitter taste of caffeine.

BACKGROUND

Caffeine has been used as a stimulant and anti-sleep aid for centuries. While the most common source of caffeine is coffee, it is also found in other natural plant sources, such as tea, cola nuts also spelled as kola nuts, yerba mate, guaranga berries, guayusa and the yaupon holly. Chemically, caffeine is 1,3,7-trimethylxanthine with systematic IUPAC name 1,3,7-trimethyl-1H-purine-2,6(3H,7H)-dione. Drinking coffee has long been recognized as a stimulant and therefore a way to increase playfulness and alertness. Many people drink coffee for its caffeine content to become fully awake and alert in the morning. In many workplaces, coffee is provided throughout the day so that people can operate at peak alertness and efficiency. Students also appreciate the benefits of coffee to help them study long into the night.

Currently caffeine is available as an "over the counter" drug in the form of capsules and tablets. However caffeine has a bitter taste and/or an unpalatable taste, making caffeine a difficult additive to capsules and tablets. Capsules and tablets have been precluded from the popularity of caffeine ingestion by the extremely bitter and unpalatable taste of caffeine.

SUMMARY

The present disclosure includes an energy tablet comprising a tablet including microencapsulated caffeine, wherein the tablet is palatable for oral consumption.

The present disclosure also includes a method of making an energy tablet, the method comprising the steps of providing caffeine in an oil based coating, flavoring agent, and sucralose, passing first step components through a screen, mixing first step components together, providing taurine, glucuronolactone, sodium starch glycolate, xanthan gum and citric acid, passing fourth step components through a second screen, blending fourth step components together with the blended first step components, providing sodium stearyl fumarate, passing sodium stearyl fumarate through a third screen, blending sodium stearyl fumarate together with the blended six step components, and compressing the blended components into a tablet creating the energy tablet.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 1 is a process flow diagram according to an embodiment of the present disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

A sweet tart energy tablet according to the present disclosure successfully masks the extreme bitter taste of caffeine. There are three components which make sweet tart energy tablet more palatable: (1) coated or microencapsulated caffeine, (2) citric acid, and (3) Prosweet®. The term "palatable," as used herein, means that the tablet of this invention has any one of the following characteristics: a taste, mouth feel, chewability, texture, aroma, and lack of grittiness and lack of bad aftertaste that makes the tablet agreeable to consume by mouth. Sweet tart energy tablet can be taken orally as a chewable tablet or can be dissolved in a drink. A 2.6 gram chewable tablet is the equivalent or comparable to an 8 ounce energy drink or a 2 ounce energy shot.

The exemplary embodiment contemplates microencapsulated caffeine in a solid tablet coating. However, semi-solid coatings (such as gelatin) or liquid coatings (including lipophilic base formulations such as soy bean oil, triglycerides, veg. oil, or hydrophilic base formulations such as poly ethylene glycol, hydroxypropyl methyl cellulose, hydroxypropyl cellulose, or polyvinylpyrrolidone) could also be used. Other commonly known techniques for solvating the medicament such as suspensions, liquids, powders, pills, capsules, suppositories, or the like could be used.

Typically, microcapsulated caffeine (also generally described as microcapsules or microparticles) are sized to be generally less than about 1 mm in size, preferably less than about 0.8 mm, less than about 0.7 mm, less than about 0.6 mm, less than about 0.5 mm, less than about 0.4 mm, less than about 0.3 mm, less than about 0.2 mm, or less than about 0.1 mm. In further embodiments, microparticles can be less than about 50 µm, less than about 40 µm, less than about 30 µm, less than about 20 µm, less than about 10 µm, or less than about 1 µm. In certain embodiments, microparticles have sizes in the range of about 0.2 mm to about 2 mm, about 0.3 mm to about 1.5 mm, about 0.4 mm to about 1 mm, or about 0.5 mm to about 1 mm. In a specific embodiment, microparticles are sized such that at least 80% of microparticles are less than 0.7 mm in size. In other embodiments, microparticles are sized such that less than or equal to 20% of microparticles are retained on a 20 mesh screen. In still further embodiments, microparticles are of a size making the particles essentially or completely undetectable by a consumer of a product incorporating such particles. In such embodiments, microparticles can have average sizes in the range of about 1 µm to about 0.8 mm, about 10 µm to about 0.7 mm, about 0.1 mm to about 0.7 mm, about 0.2 mm to about 0.7 mm, or about 0.3 mm to about 0.6 mm. In on specific embodiment, microparticles have an average size of 0.4 mm to about 0.8 mm or about 0.6 mm.

Specifically, fine microparticles are described as a batch of particles wherein no more than ten percent (10%) of the particles are less than about one hundred and fifty microns (150 µm) and no more than twenty percent (20%) of the particles are greater than about seven hundred and ten microns (710 µm). The control of fine microparticles is one of many factors to obtain a palatable tablet according to an embodiment of the present disclosure. One of ordinary skill in the art is aware of using other factors, such as the use of different coatings or increased tablet compression, to obtain a palatable tablet according to an embodiment of the present disclosure.

Particle size may be adjustable such that a tablet prepared therewith can exhibit any sort of texture from a mildly grainy effect (which may be desirable in some applications) to practically no noticeability of the presence of microparticles. In specific embodiments, the microencapsulated caffeine is of a sufficient small particle size such that the presence of the microcapsules is not recognizable to the average human consumer. Coated or microencapsulated particles useful according to the present disclosure are preferably palatable for consumption and suitable for incorporation into food or beverages and unaffected by food or beverage preparation, as well as capable of incorporation into ancillary material, such as confections, or a filling material.

Caffeine particle size control is beneficial to achieve content uniformity. The appropriate grade or level of coating is also beneficial to the product. If an improper particle size is used, the content uniformity could be unacceptable resulting in super potent or subpotent product being manufactured. For example, if greater than about twenty-five percent (25%) of the caffeine particles are larger than 0.7 mm, some tablets could be superpotent and some subpotent. If an improper grade or coated level of caffeine is used, a user may be able to detect the bitter taste of caffeine which results in a product which is less palatable. For example if greater than about 10% of the caffeine particles are less than 0.15 mm, the bitter taste could be detected.

Microparticles can vary in relation to the overall content of the encapsulated material. Preferably, microparticles used according to the present disclosure comprise predominately the encapsulated material; however lesser contents can be acceptable. In certain embodiments, microparticles comprise about 10% by weight caffeine, based on the overall weight of microparticles, about 20% by weight caffeine, about 30% by weight caffeine, about 40% by weight caffeine, about 50% by weight caffeine, about 55% by weight caffeine, about 60% by weight caffeine, about 65% by weight caffeine, about 70% by weight caffeine, about 80% by weight caffeine, or about 90% by weight caffeine based on the overall weight of microparticles. In a specific embodiment, microparticles comprise about 10% to about 90% by weight caffeine, about 20% to about 80% by weight caffeine, about 30% to about 70% by weight caffeine, about 30% to about 60% by weight caffeine, or about 40% to about 60% by weight caffeine.

Thus, food or beverage products of the present disclosure can comprise a component that includes microencapsulated caffeine. Citric acid and fruit flavor provide the "Sweet Tart" like product. Prosweet® is sold by manufacturer, Virginia Dare, 882 Third Avenue, Brooklyn, N.Y. 11232, Phone: 718-788-1776, website: www.virginiadare.com. Prosweet® has been selected as a sweetening agent and bitter masking agent. These components are also beneficial in masking the bitter caffeine flavor.

The process of manufacturing the sweet tart energy tablet is as follows:

Step #1: Several components are acquired or prepared. Microencapsulated caffeine has been purchased from manufacturer, Maxx Performance Inc. 3621 Aerial Way Drive Roanoke, Va. 24018 Phone: (540) 904-6657 website: www-.maxxperform.com/. In addition to Maxx Performance, Inc., several additional companies presently provide services in the field of microencapsulation and would be expected to be capable of preparing microencapsulated caffeine to meet the physical parameters described herein. For example, Watson, Inc. (West Haven Conn.), Southwest Research Institute (San Antonio, Tex.), and GAT Food Essentials, GmbH (Ebenfurth, Austria) are examples of companies specializing in microencapsulation technologies, particularly for use in the food industry. A skilled person, armed with the present disclosure, would be expected to be capable of preparing microencapsulated caffeine for use in the present invention by using manufacturing methods provided by such companies.

Specifically microencapsulated caffeine is acquired from Maxx Performance in a hydrogenated vegetable oil solution, preferably soy bean oil at 50%. While it is disclosed that microencapsulated caffeine can be purchased, it is also envisioned that one of ordinary skill in the art could use a process to microencapsulate caffeine as part of the steps of manufacturing a sweet tart energy tablet according to an embodiment of the present disclosure.

A microcapsule is a coating around a small amount of particle or droplet. For example a microcapsule may comprise a small sphere with a uniform coating thickness around a material. In this example, the material inside sphere is typically referred to as a core, internal phase or fill, whereas the microcapsule may be described as a shell, coating and/or membrane. Not all microcapsules fit the small sphere example. The microcapsule may coat a jagged particle, an emulsion, a suspension of solids or a suspension of other microcapsules. For example microcapsules may comprise a plurality of coatings, shells, or membranes.

The process of microencapsulation may comprise physical, physio-chemical, or chemical methods. Physio-chemical methods include ionotropic gelation and coacervation phase separation.

Physical methods of encapsulation could be used, such as spray coating, pan coating, fluid bed coating, annular jet coating, spinning disk atomization, spray cooling, centrifugal extrusion, vibrational nozzle (which is also described as microgranulation or matrix-encapsulation), spray drying, spray chilling, stationary nozzle coextrusion, centrifugal head coextrusion, air-suspension coating, or submerged nozzle coextrusion.

Microencapsulated caffeine according to the present disclosure could be formed using any of various chemical encapsulation techniques such as solvent evaporation, solvent extraction, organic phase separation, interfacial polymerization, simple and complex coacervation, in-situ polymerization, liposome encapsulation, and nanoencapsulation.

Microcapsules are commercially available, and exemplary types of microcapsule technologies are of the type set forth in Gutcho, Microcapsules and Microencapsulation Techniques (1976); Gutcho, Microcapsules and Other Capsules Advances Since 1975 (1979); and Kondo, Microcapsule Processing and Technology (1979), all of which are incorporated herein by reference.

Controlling the particle size of microencapsulated caffeine and the ratio of caffeine to oil are beneficial to producing an appropriate finished product. It is beneficial to provide microencapsulated caffeine within the range of approximately 100 to approximately 800 microns. It is also beneficial to provide a caffeine to oil ratio of approximately 50% calculated on a weight/weight basis.

Sweetening agents such as sucralose, saccharin, a fluourinated sucrose derivative, acesulfame potassium and aspartame. A sweetening agent can also be used to enhance to taste of the tablet, making the tablet more palatable than a tablet without a sweetening agent. Sweetening agents include natural sugars and artificial sugar substitutes.

Chemically, sucralose is 4,1',6'-trichloro-4,1',6'-trideoxy-galactosucrose. Sucralose is a novel non-nutrition sweetener with high sweetness that is approximately 600 times as sweet as sucrose. Sucralose has been permitted by more than twenty countries to be used as a food sweetener because it does not participate in metabolism, is not absorbed by human body, is not utilized by the dental caries bacteria, or does not cause dental caries.

Flavoring agents such as Prosweet® flavor agents are also acquired. Flavoring agents mean any flavor masking agents in the nature of chemical products for use in the manufacture of foods, beverages, candies, tablets and chewing products. A flavoring agent can be used to enhance the taste of the tablet, making the tablet more palatable than a tablet without a flavoring agent. Some flavoring agents such as spray dried flavor agents are beneficial because they are easy to incorporate into a chewable tablet. Flavoring agents are readily available from many commercial sources. Several flavors and flavoring agents suitable for the tablet would be well known to those skilled in the art in view of the present disclosure.

Non-limiting examples of the amount of sweetening agents and/or flavoring agents that can be used in the tablet composition of the present invention are listed in Table 1. The exemplary amounts in Table 1 are given as percentage of the total tablet weight.

Step #2: components of Step #1 are sieved through a screen. As illustrated in FIG. 1, the screen is shown to be a hand screen with a 20 mesh (0.0331 inch, 841 micron, 0.841 millimeter) screen size. It is envisioned that screens of multiple sizes and multiple screens can be used.

Step #3: The sweetening agents are mixed and blended with the bitter component. Micro-encapsulated caffeine is blended with sucralose, Prosweet® and flavor to achieve intimate mixing. Although microencapsulated, the microencapsulated caffeine could potentially retain a residual bitter flavor. The process of microencapsulating is considered to reduce but not eliminate the bitter and unpalatable taste of caffeine. Several factors play into the amount of reduction such as the content of caffeine in the microcapsule and/or the sensitivity of the taster. Prosweet® is beneficial to remove a considerable amount of the residual bitterness.

Step #3 mixing can be accomplished by any suitable means known by any one of ordinary skill in the art. As illustrated in FIG. 1, the step #3 mixing occurs in a 700 L V-blender for approximately 30 minutes at approximately 12 revolutions per minute.

Step #4 illustrates the acquisition of additional components including taurine, glucuronolactone, vitamin B6, vitamin B12, sorbitol, sodium starch glycolate, colorant, xanthan gum and citric acid. Sorbitol is used as a sugar substitute. Sorbitol may be referred to as a nutritive sweetener because sorbitol provides dietary energy: 2.6 kilocalories (11 kilojoules) per gram.

Taurine is a conditionally essential amino acid but it is found in a free form and many tissues, particularly muscle and nerve. As a reducer of peripheral sympathetic activity, taurine may counteract the unpleasant effects of caffeine without inhibiting the beneficial stimulating effects of caffeine.

Sodium starch glycolate is a disintegrant which assists in dissolving the tablet when dropped in a drink. Disintegrant is typically defined as substance which expands and disintegrates causing a component to break apart. More specifically, disintegrant can mean for this action to occur in a digestive tract thereby releasing active ingredients for absorption by the digestive tract.

Sorbitol is an additional component. Sorbitol is primarily a diluent. Sorbitol has a sweetening effect, it is sugar free and sorbitol provides a tablet with acceptable friability. Friability is generally defined as the ability of a solid substance to be reduced to smaller pieces with little effort. An appropriate grade of sorbitol within a particle size range is beneficial to achieve acceptable content uniformity. By appropriate grade within a particle size range means within the range of effective particle sizes such as the range of approximately 60 microns to approximately 600 microns. The appropriate grade of sorbitol assists in ensuring that the finished product does not have excess caffeine in some tablets and subpotent caffeine in other tablets. The appropriate grade of sorbitol also provides an appealing mouth feel, such as a non-gritty texture.

Citric acid and fruit flavor provide the "Sweet Tart" like product. These components are also beneficial in masking the bitter caffeine flavor.

Additional components may impart chewable and palatable characteristics to the tablet and are envisioned to be suitable for human consumption, that is, free of harmful amounts of any toxins or components that are adverse to humans. All ingredients in the tablet should be generally recognized as safe (GRAS), as determined by the Food and Drug Administration (FDA) or the Flavor and Extract Manufacturers' Association (FEMA). The additional components selected for the invention should be chewable either individually or in combination. The additional components should not confer a disagreeable taste to the tablet. Thus, the additional components should be palatable. The ingredients of additional components may include one or more diluents. Many diluents or other ingredients suitable as components of carriers for a chewable, palatable tablet including micro-encapsulated caffeine are available and would be well known to those skilled in the art in view of the present disclosure.

Step #5: components of Step #4 are filtered through a screen. As illustrated in FIG. 1, the screen is shown to be a hand screen with a 8 mesh (0.0937 inch, 2.36 millimeter) screen size. It is envisioned that screens of multiple sizes and multiple screens can be used.

Step #6: The components of Step #4 are added to the mixture of Step #3. The citric acid and fruit flavor components are beneficial to mask the bitter caffeine flavor. Step #6 mixing can be accomplished by any suitable means known by any one of ordinary skill in the art. As illustrated in FIG. 1, the step #6 mixing occurs after Step #3 mixing in the 700 L V-blender for approximately 15 minutes at approximately 12 revolutions per minute.

Step #7: Sodium stearyl fumarate is acquired. Sodium stearyl fumarate is used as the lubricant. For the purposes of this disclosure, sodium stearyl fumarate sold under the trademark Lubripharm® has been selected as an exemplary embodiment. Sodium stearyl fumarate was selected because of its solubility relative to other dry lubricants. Sodium stearyl fumarate was also selected because it did not produce a film on top of a drink when a tablet was dissolved in the drink.

Step #8: Sodium stearyl fumarate is passed through a screen. As illustrated in FIG. 1, the screen is shown to be a hand screen with a 20 mesh (1.04 millimeter) screen size. It is envisioned that screens of multiple sizes and multiples screens can be used.

Step #9: Sodium stearyl fumarate is added to the mixture of Step #6. Step #9 mixing can be accomplished by any suitable means known by any one of ordinary skill in the art. As illustrated in FIG. 1, the Step #9 mixing occurs after Step #6 mixing in the 700 L V-blender for approximately 5 minutes at approximately 12 revolutions per minute.

Step #10: The final blend of step #9 is compressed into a tablet using a Rotary Tablet Press Machine (ZPW-17) Shanghai Develop Machinery Co., Limited, NO28 LANE 479 EAST WUWEI ROAD SHANGHAI CHINA 200333, telephone: +86-21-62657914, fax: 86-21-51062082, website: shdevelopmachinery.en.alibaba.com. The compressed tablet weighs approximately 2.6 grams and has tablet hardness within the range of approximately 10 kiloponds and approximately 20 kiloponds. The compressed tablet is a sweet tart energy tablet according to an embodiment of the present disclosure.

Optional Step #11: The sweet tart energy tablet is passed through a tablet deduster to ensure that all excess powder or blend is removed from the tablet prior to packaging.

TABLE 1

Range of flavored formulations for sweet tart energy tablet
Flavored Formulations

|  | mg/tab | kg/batch | % w/w |
|---|---|---|---|
| Caffeine/soy bean oil (50%) | 160 | 10.4 | 6.371963 |
| Vitamin B6 | 20 | 1.3 | 0.796495 |
| B12 1% concentration | 2.5 | 0.163 | 0.099562 |
| Taurine | 500 | 32.5 | 19.91239 |
| Glucuronolactone | 250 | 16.25 | 9.956193 |
| Sorbitol | 1300 | 84.5 | 51.7722 |
| Xanthan Gum | 25 | 1.625 | 0.995619 |
| Sucralose | 35 | 2.275 | 1.393867 |
| Sodium Starch Glycolate | 100 | 6.5 | 3.982477 |
| Citric Acid | 50-81 |  | 1.9-3.1 |
| Prosweet ® MM50 | 100 | 6.5 | 3.982477 |
| Flavoring (fruit flavor) | 26-40 |  | 1.0-1.5 |
| Color Agent | 0.09-3.25 |  | 0.003-0.12 |
| Sodium Stearyl Fumarate (Pruv ®) | 18.5 | 1.203 | 0.736758 |
| Total | 2587.09-2635.25 | — | 100 |

TABLE 1A

Orange formulation for sweet tart energy tablet
Orange Formulation

|  | mg/tab | kg/batch | % w/w |
|---|---|---|---|
| Caffeine/soy bean oil (50%) | 160 | 10.4 | 6.132617861 |
| Vitamin B6 | 20 | 1.3 | 0.766577233 |
| B12 1% concentration | 2.5 | 0.163 | 0.095822154 |
| Taurine | 500 | 32.5 | 19.16443082 |
| Glucuronolactone | 250 | 16.25 | 9.582215408 |
| Sorbitol | 1300 | 84.5 | 49.82752012 |
| Xanthan Gum | 25 | 1.625 | 0.958221541 |
| Sucralose | 35 | 2.275 | 1.341510157 |
| Sodium Starch Glycolate | 100 | 6.5 | 3.832886163 |
| Citric Acid | 65 | 4.225 | 2.491376006 |
| Prosweet ® MM50 | 100 | 6.5 | 3.832886163 |
| Flavoring (Orange) | 31.5 | 2.0475 | 1.207359141 |

TABLE 1A-continued

Orange formulation for sweet tart energy tablet
Orange Formulation

|  | mg/tab | kg/batch | % w/w |
|---|---|---|---|
| Color Agent (Yellow) | 1.5 | 0.0975 | 0.057493292 |
| Sodium Stearyl Fumarate (Pruv ®) | 18.5 | 1.203 | 0.70908394 |
| Total | 2609 | 169.586 | 100 |

TABLE 1B

Strawberry flavored formulation for sweet tart energy tablet
Strawberry Formulation

|  | mg/tab | kg/batch | % w/w |
|---|---|---|---|
| Caffeine/soy bean oil (50%) | 160 | 10.4 | 6.125035 |
| Vitamin B6 | 20 | 1.3 | 0.765629 |
| B12 1% concentration | 2.5 | 0.163 | 0.095704 |
| Taurine | 500 | 32.5 | 19.14073 |
| Glucuronolactone | 250 | 16.25 | 9.570367 |
| Sorbitol | 1300 | 84.5 | 49.76591 |
| Xanthan Gum | 25 | 1.625 | 0.957037 |
| Sucralose | 35 | 2.275 | 1.339851 |
| Sodium Starch Glycolate | 100 | 6.5 | 3.828147 |
| Citric Acid | 65.38 | 4.225 | 2.502842 |
| Prosweet ® MM50 | 100 | 6.5 | 3.828147 |
| Flavoring (Strawberry) | 34.2 | 2.0475 | 1.309226 |
| Color Agent (Red Lake) | 1.65 | 0.0975 | 0.063164 |
| Sodium Stearyl Fumarate (Pruv ®) | 18.5 | 1.203 | 0.708207 |
| Total | 2612.23 | 169.586 | 100 |

TABLE 1C

Black Cherry flavored formulation for sweet tart energy tablet
Black Cherry Formulation

|  | mg/tab | kg/batch | % w/w |
|---|---|---|---|
| Caffeine/soy bean oil (50%) | 160 | 10.4 | 6.11719 |
| Vitamin B6 | 20 | 1.3 | 0.764649 |
| B12 1% concentration | 2.5 | 0.163 | 0.095581 |
| Taurine | 500 | 32.5 | 19.11622 |
| Glucuronolactone | 250 | 16.25 | 9.558109 |
| Sorbitol | 1300 | 84.5 | 49.70217 |
| Xanthan Gum | 25 | 1.625 | 0.955811 |
| Sucralose | 35 | 2.275 | 1.338135 |
| Sodium Starch Glycolate | 100 | 6.5 | 3.823244 |
| Citric Acid | 75 | 4.225 | 2.867433 |
| Prosweet ® MM50 | 100 | 6.5 | 3.823244 |
| Flavoring (Black Cherry) | 26.5 | 2.0475 | 1.01316 |
| Color Agent (Red Lake) | 1.51 | 0.0975 | 0.057731 |
| Color Agent (Grape Lake) | 1.57 | 1.0975 | 0.060025 |
| Sodium Stearyl Fumarate (Pruv ®) | 18.5 | 1.203 | 0.7073 |
| Total | 2615.58 | 170.6835 | 100 |

TABLE 1D

Watermelon flavored formulation for sweet tart energy tablet
Watermelon Formulation

|  | mg/tab | kg/batch | % w/w |
|---|---|---|---|
| Caffeine/soy bean oil (50%) | 160 | 10.4 | 6.103446 |
| Vitamin B6 | 20 | 1.3 | 0.762931 |
| B12 1% concentration | 2.5 | 0.163 | 0.095366 |
| Taurine | 500 | 32.5 | 19.07327 |
| Glucuronolactone | 250 | 16.25 | 9.536634 |
| Sorbitol | 1300 | 84.5 | 49.5905 |
| Xanthan Gum | 25 | 1.625 | 0.953663 |
| Sucralose | 35 | 2.275 | 1.335129 |
| Sodium Starch Glycolate | 100 | 6.5 | 3.814654 |
| Citric Acid | 80.38 | 4.225 | 3.066219 |
| Prosweet ® MM50 | 100 | 6.5 | 3.814654 |
| Flavoring (fruit flavor) | 30 | 2.0475 | 1.144396 |
| Color Agent | 0.09 | 0.0975 | 0.003433 |
| Sodium Stearyl Fumarate (Pruv ®) | 18.5 | 1.203 | 0.705711 |
| Total | 2621.47 | 169.586 | 100 |

TABLE 1E

Green Apple flavored formulation for sweet tart energy tablet
Green Apple Formulation

|  | mg/tab | kg/batch | % w/w |
|---|---|---|---|
| Caffeine/soy bean oil (50%) | 160 | 10.4 | 6.175818 |
| Vitamin B6 | 20 | 1.3 | 0.771977 |
| B12 1% concentration | 2.5 | 0.163 | 0.096497 |
| Taurine | 500 | 32.5 | 19.29943 |
| Glucuronolactone | 250 | 16.25 | 9.649715 |
| Sorbitol | 1300 | 84.5 | 50.17852 |
| Xanthan Gum | 25 | 1.625 | 0.964972 |
| Sucralose | 35 | 2.275 | 1.35096 |
| Sodium Starch Glycolate | 100 | 6.5 | 3.859886 |
| Citric Acid | 50 | 4.225 | 1.929943 |
| Prosweet ® MM50 | 100 | 6.5 | 3.859886 |
| Flavoring (Green Apple) | 26.5 | 2.0475 | 1.02287 |
| Color Agent (Green Lake) | 3.25 | 0.0975 | 0.125446 |
| Sodium Stearyl Fumarate (Pruv ®) | 18.5 | 1.203 | 0.714079 |
| Total | 2590.75 | 169.586 | 100 |

TABLE 1F

Grape flavored formulation for sweet tart energy tablet
Grape Formulation

|  | mg/tab | kg/batch | % w/w |
|---|---|---|---|
| Caffeine/soy bean oil (50%) | 160 | 10.4 | 6.085386 |
| Vitamin B6 | 20 | 1.3 | 0.760673 |
| B12 1% concentration | 2.5 | 0.163 | 0.095084 |
| Taurine | 500 | 32.5 | 19.01683 |
| Glucuronolactone | 250 | 16.25 | 9.508415 |
| Sorbitol | 1300 | 84.5 | 49.44376 |
| Xanthan Gum | 25 | 1.625 | 0.950841 |
| Sucralose | 35 | 2.275 | 1.331178 |
| Sodium Starch Glycolate | 100 | 6.5 | 3.803366 |
| Citric Acid | 75 | 4.225 | 2.852524 |
| Prosweet ® MM50 | 100 | 6.5 | 3.803366 |
| Flavoring (Grape) | 40 | 2.0475 | 1.521346 |
| Color Agent (Grape Lake) | 3.25 | 0.0975 | 0.123609 |
| Sodium Stearyl Fumarate (Pruv ®) | 18.5 | 1.203 | 0.703623 |
| Total | 2629.25 | 169.586 | 100 |

TABLE 1G

Blue Raspberry flavored formulation for sweet tart energy tablet
Blue Raspberry Formulation

|  | mg/tab | kg/batch | % w/w |
|---|---|---|---|
| Caffeine/soy bean oil(50%) | 160 | 10.4 | 6.175818 |
| Vitamin B6 | 20 | 1.3 | 0.771977 |
| B12 1% concentration | 2.5 | 0.163 | 0.096497 |
| Taurine | 500 | 32.5 | 19.29943 |
| Glucuronolactone | 250 | 16.25 | 9.649715 |
| Sorbitol | 1300 | 84.5 | 50.17852 |
| Xanthan Gum | 25 | 1.625 | 0.964972 |
| Sucralose | 35 | 2.275 | 1.35096 |
| Sodium Starch Glycolate | 100 | 6.5 | 3.859886 |
| Citric Acid | 50 | 4.225 | 1.929943 |
| Prosweet ® MM50 | 100 | 6.5 | 3.859886 |
| Flavoring (Blue Raspberry) | 26.5 | 2.0475 | 1.02287 |
| Color Agent (Blue Lake) | 3.25 | 0.0975 | 0.125446 |
| Sodium Stearyl Fumarate (Pruv ®) | 18.5 | 1.203 | 0.714079 |
| Total | 2590.75 | 169.586 | 100 |

In a second embodiment of the present disclosure there is an unflavored version specifically designed for use in drinks. All of the statements regarding the flavored formulation apply to this unflavored version.

Furthermore, the unflavored version is configured to be dissolved in a drink and consumed. The unflavored version can be used in both alcoholic and nonalcoholic beverages.

The unflavored version is not configured to alter the taste. It is envisioned that the coating material used in forming the microencapsulated caffeine is also preferably useful for masking the bitterness typically associated with caffeine. In certain embodiments, the coating material is a material that has the capability to render the encapsulated caffeine essentially tasteless. In other embodiments, the microencapsulation coating material is a material that is itself substantially or completely tasteless. Thus, the microencapsulation coating material can be described as a material that substantially or completely masks or blocks the bitter taste of caffeine.

The unflavored version is configured to provide the benefit of the energy. Palatable components of citric acid and Prosweet®, do not necessarily apply to the unflavored version. The method of manufacturing the sweet tart energy tablet is similar to the method of manufacturing the unflavored version.

Many drinks that can include the unflavored version including microencapsulated caffeine according to the disclosure are subject to high temperatures (e.g., hot coffee, hot tea). Thus, it is beneficial for the microencapsulated caffeine to be formed with a coating material that is thermostable, preferably meaning it can withstand the high temperatures of drink preparation (i.e., in the range of 100° C. to 200° C.) and the extended elevated temperatures of drink consumption without melting, degrading, or otherwise exposing the contents of the microcapsule. In certain embodiments, the microencapsulation coating material comprises a material that is thermostable up to a temperature of at least about 80° C., at least about 90° C., at least about 100° C., at least about 110° C., or at least about 120° C.

The thermostability of the material can also be a function of time. Accordingly, the coating materials of the invention can include materials that are thermostable up to even greater temperatures when only exposed to the temperature for a relatively short time. For example, a coating material useful according to the invention can be thermostable up to a temperature of about 200° C. for a time of at least about 10 minutes, at least about 5 minutes, or at least about 3 minutes. Conversely, the coating materials of the invention can include materials that are thermostable up to even greater periods of time when exposed to elevated temperatures.

Still further, the unflavored version provides a process for dosing a food or beverage with a predetermined amount of caffeine. In one embodiment, the process comprises providing caffeine in a component for use in preparing a food or beverage such that a known mass or volume of said component comprises a predetermined amount of caffeine. The component can then be used in preparing the food or beverage so as to provide a food or beverage having an amount of caffeine within a predetermined concentration range, such as described herein. As previously noted, the caffeine can be a stand-alone product such that a known mass or volume of the product is known to contain a predetermined concentration of caffeine. Likewise, the caffeine can be in a pre-mixed component such that a known mass or volume of the pre-mix is known to contain a predetermined concentration of caffeine. This is particularly useful to avoid overdosing of the caffeine and to be able to equate the caffeine content of a serving of the food or beverage to other known caffeinated items. For example, a single cup of a beverage could be dosed to incorporate a concentration of caffeine equivalent to the concentration of caffeine found in an average cup of coffee.

TABLE 2

Unflavored formulation for energy tablet
Flavorless Formulation

|  | mg/tab | % w/w |
|---|---|---|
| Caffeine/soybean oil (50%) | 0.16 | 6.704379 |
| Vitamin B6 | 0.04 | 1.676095 |
| Vitamin B12 1% concentration | 0.005 | 0.104756 |
| Taurine | 0.5 | 20.95118 |
| Glucuronolactone | 0.25 | 10.47559 |
| Sorbitol | 1.3 | 54.47308 |
| Sodium Starch Glycolate | 0.115 | 4.818772 |
| Sodium Stearyl Fumarate (Pruv ®) | 0.019 | 0.796145 |
| Total | 2.3865 | 100 |

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. An energy tablet comprising:
   a chewable tablet including microencapsulated caffeine in an oil based coating, the tablet including either a flavored tablet or an unflavored tablet, the flavored tablet including:
   microencapsulated caffeine in fifty percent soy bean oil, wherein the caffeine in fifty percent soy bean oil is approximately 6% w/w, vitamin B6 is approximately 0.7% w/w,
   vitamin B12 at 1% concentration is approximately 0.095% w/w to approximately 0.099% w/w,
   taurine is approximately 19% w/w to approximately 19.9% w/w,
   glucuronolactone is approximately 9.5% w/w to approximately 9.9% w/w,
   sorbitol is approximately % 49.4% w/w to approximately 51.7% w/w,
   xanthan gum is approximately 0.95% w/w to approximately 0.99% w/w,
   sucralose is approximately 1.3% w/w,
   sodium starch glycolate is approximately 3.8% w/w to approximately 3.98% w/w,
   citric acid is approximately 1.9% w/w to approximately 3.1% w/w, and
   sodium stearyl fumarate is approximately 0.7% w/w of the weight of the tablet;
   the unflavored tablet comprising:
   microencapsulated caffeine in fifty percent soy bean oil, wherein the caffeine in fifty percent soy bean oil is approximately 6.7% w/w,
   vitamin B6 is approximately 1.6% w/w,
   vitamin B12 at 1% concentration is approximately 0.1% w/w,
   taurine is approximately 20.95% w/w,
   glucuronolactone is approximately 10.4% w/w,
   sorbitol is approximately 54% w/w,
   sodium starch glycolate is approximately 4.8% w/w, and
   sodium stearyl fumarate is approximately 0.7% w/w of the weight of the tablet,
   wherein the tablet is palatable for oral consumption.

2. The tablet of claim 1 wherein the flavored tablet includes sweetening agents in an amount effective to make the tablet palatable.

3. The tablet of claim 2 wherein the sweetening agents include at least one flavoring agent.

4. The tablet of claim 2 wherein the sweetening agents include sucralose.

5. The tablet of claim 1 wherein the tablet has a sweet tart taste.

6. The tablet of claim 1 wherein the microencapsulated caffeine is soluble in a lipophilic base.

7. The tablet of claim 1 wherein the oil based coating is vegetable oil.

8. The tablet of claim 7 wherein the vegetable oil includes soybean oil.

9. The tablet of claim 1 wherein the microcapsulated caffeine is sized to be within the range of approximately 0.7 mm to about 1 mm.

10. The tablet of claim 1 wherein the tablet is created by direct compression.

11. The tablet of claim 1 wherein the tablet is malleable.

12. The tablet of claim 1 wherein the tablet hardness is within the range of approximately 17 kiloponds and approximately 20 kiloponds.

13. The tablet of claim 1 consisting of:
a chewable tablet including microencapsulated caffeine in an oil based coating, the tablet consisting of either a flavored tablet or an unflavored tablet,
the flavored tablet consisting of:
microencapsulated caffeine in fifty percent soy bean oil, wherein the caffeine in fifty percent soy bean oil is approximately 6% w/w, vitamin B6 is approximately 0.7% w/w,
vitamin B12 at 1% concentration is approximately 0.095% w/w to approximately 0.099% w/w,
taurine is approximately 19% w/w to approximately 19.9% w/w,
glucuronolactone is approximately 9.5% w/w to approximately 9.9% w/w,
sorbitol is approximately 49.4% w/w to approximately 51.7% w/w,
xanthan gum is approximately 0.95% w/w to approximately 0.99% w/w,
sucralose is approximately 1.3% w/w,
sodium starch glycolate is approximately 3.8% w/w to approximately 3.98% w/w,
citric acid is approximately 1.9% w/w to approximately 3.1% w/w,
sodium stearyl fumarate is approximately 0.7% w/w of the weight of the tablet, and a flavoring agent selected from the group consisting of orange, strawberry, fruit, black cherry, grape, blue raspberry, green apple, or combinations thereof, wherein the flavoring agent is approximately 1% w/w of the weight of the tablet,
a color agent selected from the group consisting of yellow, red lake, grape lake, blue lake, green lake, or combinations thereof, wherein the color agent is no more than approximately 0.12% w/w of the weight of the tablet;
the unflavored tablet comprising:
microencapsulated caffeine in fifty percent soy bean oil, wherein the caffeine in fifty percent soy bean oil is approximately 6.7% w/w,
vitamin B6 is approximately 1.6% w/w,
vitamin B12 at 1% concentration is approximately 0.1% w/w,
taurine is approximately 20.95% w/w,
glucuronolactone is approximately 10.4% w/w,
sorbitol is approximately 54% w/w,
sodium starch glycolate is approximately 4.8% w/w, and
sodium stearyl fumarate is approximately 0.7% w/w of the weight of the tablet.

14. The tablet of claim 1, wherein the flavored tablet further comprises a flavoring agent selected from the group consisting of orange, strawberry, fruit, black cherry, grape, blue raspberry, green apple, or combinations thereof, wherein the flavoring agent is approximately 1% w/w of the weight of the tablet.

15. The tablet of claim 1 further comprising a color agent selected from the group consisting of yellow, red lake, grape lake, blue lake, green lake, or combinations thereof, wherein the color agent is no more than approximately 0.12% w/w of the weight of the tablet.

16. The tablet of claim 1 consisting essentially of:
a chewable tablet including microencapsulated caffeine in an oil based coating, the tablet consisting of either a flavored tablet or an unflavored tablet,
the flavored tablet consisting essentially of microencapsulated caffeine in fifty percent soy bean oil, wherein the caffeine in fifty percent soy bean oil is approximately 6% w/w, vitamin B6 is approximately 0.7% w/w,
vitamin B12 at 1% concentration is approximately 0.095% w/w to approximately 0.099% w/w,
taurine is approximately 19% w/w to approximately 19.9% w/w,
glucuronolactone is approximately 9.5% w/w to approximately 9.9% w/w,
sorbitol is approximately 49.4% w/w to approximately 51.7% w/w,
xanthan gum is approximately 0.95% w/w to approximately 0.99% w/w,
sucralose is approximately 1.3% w/w,
sodium starch glycolate is approximately 3.8% w/w to approximately 3.98% w/w,
citric acid is approximately 1.9% w/w to approximately 3.1% w/w,
sodium stearyl fumarate is approximately 0.7% w/w of the weight of the tablet, and a flavoring agent selected from the group consisting of orange, strawberry, fruit, black cherry, grape, blue raspberry, green apple, or combinations thereof, wherein the flavoring agent is approximately 1% w/w of the weight of the tablet,
a color agent selected from the group consisting of yellow, red lake, grape lake, blue lake, green lake, or combinations thereof, wherein the color agent is no more than approximately 0.12% w/w of the weight of the tablet;
the unflavored tablet comprising:
microencapsulated caffeine in fifty percent soy bean oil, wherein the caffeine in fifty percent soy bean oil is approximately 6.7% w/w,
vitamin B6 is approximately 1.6% w/w,
vitamin B12 at 1% concentration is approximately 0.1% w/w,
taurine is approximately 20.95% w/w,
glucuronolactone is approximately 10.4% w/w,
sorbitol is approximately 54% w/w,
sodium starch glycolate is approximately 4.8% w/w, and
sodium stearyl fumarate is approximately 0.7% w/w of the weight of the tablet.

* * * * *